United States Patent
Zhang

(10) Patent No.: US 11,914,640 B2
(45) Date of Patent: Feb. 27, 2024

(54) ADDING SYSTEM FOR ADDING SCENT INFORMATION TO DIGITAL PHOTOGRAPHS, AND ADDING METHOD FOR USING THE SAME

(71) Applicant: Hengzhong Zhang, Taichung (TW)

(72) Inventor: Hengzhong Zhang, Taichung (TW)

( * ) Notice: Subject to any disclaimer, the term of this patent is extended or adjusted under 35 U.S.C. 154(b) by 103 days.

(21) Appl. No.: 17/205,829

(22) Filed: Mar. 18, 2021

(65) Prior Publication Data
US 2021/0209153 A1 Jul. 8, 2021

Related U.S. Application Data

(63) Continuation of application No. PCT/CN2018/106757, filed on Sep. 20, 2018.

(51) Int. Cl.
*G06F 16/583* (2019.01)
*G06F 3/01* (2006.01)
(Continued)

(52) U.S. Cl.
CPC ............ *G06F 16/583* (2019.01); *G06F 3/012* (2013.01); *G06F 3/013* (2013.01); *G06F 3/017* (2013.01); *G06F 3/04842* (2013.01); *G06F 3/167* (2013.01); *G06F 16/972* (2019.01); *G06V 40/172* (2022.01)

(58) Field of Classification Search
CPC ...... G06F 16/583; G06F 16/972; G06F 3/012; G06F 3/013; G06F 3/017; G06F 3/04842; G06F 3/167; G06V 40/172
See application file for complete search history.

(56) References Cited

U.S. PATENT DOCUMENTS 5,949,522 A * 9/1999 Manne ................ A61L 9/122
    261/DIG. 65
6,024,783 A * 2/2000 Budman ............. H04N 7/08
    261/DIG. 65
(Continued)

FOREIGN PATENT DOCUMENTS

| CN | 101459768 A | 6/2009 |
| CN | 105164614 A | 12/2015 |
| CN | 107563906 A | 1/2018 |

*Primary Examiner* — Sang H Kim
(74) *Attorney, Agent, or Firm* — Muncy, Geissler, Olds & Lowe, P.C.

(57) ABSTRACT

An adding system for adding scent information to digital-photographs includes an application program installed in an electronic device and a database stored with multiple pieces of scent information. An adding method includes following steps: loading and opening a digital-photograph through the application program; locating for a pixel point upon the digital-photograph which received an external clicking; searching boundaries outwardly from the pixel point to determine a tagged range; selecting one piece of scent information to be added from the database; linking the tagged range with the selected scent information for generating a tagged digital-photograph; and storing or sending the tagged digital-photograph. By using the adding system and adding method, other users may use other electronic devices to open the tagged digital-photograph and control a scent diffusing device to diffuse corresponding scent based on the scent information added in the digital-photograph.

17 Claims, 15 Drawing Sheets

(51) Int. Cl.
*G06F 3/0484* (2022.01)
*G06F 3/04842* (2022.01)
*G06F 3/16* (2006.01)
*G06F 16/958* (2019.01)
*G06K 9/00* (2022.01)
*G06V 40/16* (2022.01)

(56) References Cited

U.S. PATENT DOCUMENTS

| | | | | |
|---|---|---|---|---|
| 6,337,925 | B1* | 1/2002 | Cohen | G06T 7/194 |
| | | | | 382/199 |
| 9,324,004 | B2* | 4/2016 | Boncyk | G06F 16/5866 |
| 9,942,440 | B2* | 4/2018 | Kurzhanskiy | H04N 1/3873 |
| 2004/0077424 | A1* | 4/2004 | Murphy | H04N 5/225 |
| | | | | 348/E5.042 |
| 2008/0152231 | A1* | 6/2008 | Gokturk | G06Q 30/08 |
| | | | | 382/209 |
| 2010/0278424 | A1* | 11/2010 | Warner | G06F 3/04842 |
| | | | | 382/173 |
| 2016/0232131 | A1 | 8/2016 | Liu et al. | |
| 2017/0112666 | A1* | 4/2017 | Fateh | A62B 18/00 |
| 2018/0124271 | A1* | 5/2018 | Goldberg | H04N 1/32128 |
| 2019/0025773 | A1* | 1/2019 | Yang | G06N 3/045 |

* cited by examiner

ADDING SYSTEM FOR ADDING SCENT INFORMATION TO DIGITAL PHOTOGRAPHS, AND ADDING METHOD FOR USING THE SAME

TECHNICAL FIELD

The present disclosure relates to an adding system and an adding method, specifically an adding system and an adding method for adding scent information to digital photographs.

BACKGROUND

The general public usually preserves the beauty they see through photographs. However, physical photographs are limited to the preservation of the visual experience and does not include the olfactory experience.

In recent years, some companies have introduced specialized printers and proprietary inks, allowing users to print physical photographs with unique scents. However, such physical photographs use proprietary ink to continuously emit scents, and the users cannot control the emission time, emission duration and the emission field of scents. As a result, such physical photographs are inconvenient to users, and the retention time of scents is also quite short.

Alternatively, with the rapid development of the Internet, the demand for physical photograph prints has significant reduced. Instead, the general public utilizes digital photographs and store them in various types of digital devices. Therefore, a novel technology that allows users to add corresponding scents to digital photographs at will should be available on the market, to further optimize the user experience of digital photographs.

SUMMARY

The main purpose of the present disclosure is to provide a system and method for adding scent information to digital photographs, which can create digital photographs with scent information added and further store or send them.

To achieve the above purpose, the adding system of the present disclosure includes an application program installed in an electronic device and a database storing plural scent information. The adding method includes the following steps: the electronic device loads and opens a digital photograph through the application program; locates a pixel that has been externally clicked on the digital photograph; searches for the boundary from the pixel to determine a tagged range; obtains the scent information to be added from the database; links the tagged range with the scent information; and stores or sends the tagged digital photograph.

Compared with related technologies, the technical effect of the present disclosure is that one user can utilize the present disclosure to create a digital photograph with scent information, and another user can utilize another electronic device to open that digital photograph and further control a scent diffusion device to diffuse the corresponding scent based on the scent information added to the digital photographs. In this way, the user can have both visual and olfactory experiences of the digital photographs.

DETAILED DESCRIPTION

For a preferred embodiment with the drawings, the detailed description is as follows.

Figure 1:
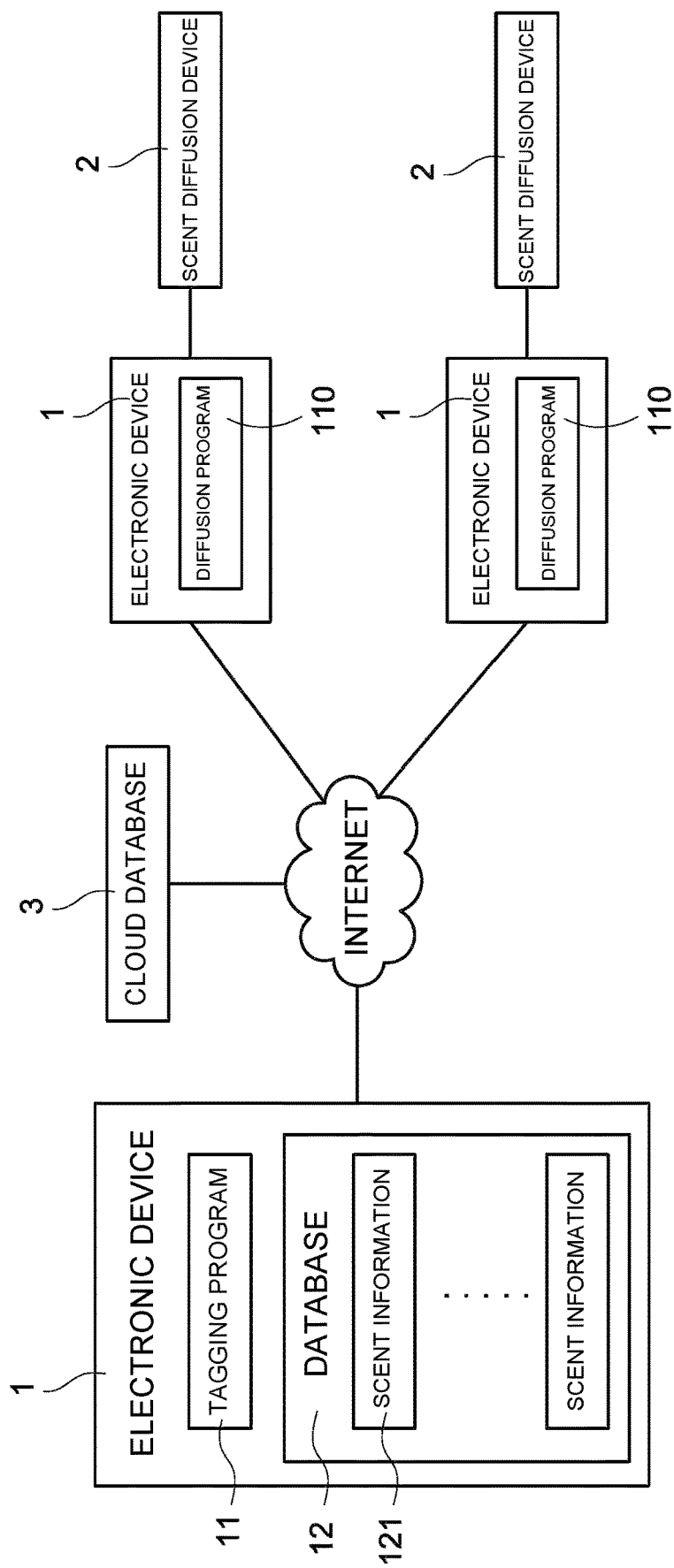
FIG. 1 is the first embodiment of the schematic diagram of the scent information adding system.

FIG. 1 is the first embodiment of the schematic diagram of the scent information adding system of the present disclosure. The present disclosure discloses an adding system that can add scent information to digital photographs (hereinafter referred to as adding system). The adding system mainly includes a tagging program 11 installed and executed in an electronic device 1 (for example, a first electronic device) and a database 12 storing a plurality of preset scent information 121. In the embodiment of FIG. 1, the database 12 is provided in the electronic device 1. In other embodiments, the database 12 can be integrated with the tagging program 11 or be independent of the electronic device 1, by way of example and not as a limitation.

Figure 4:
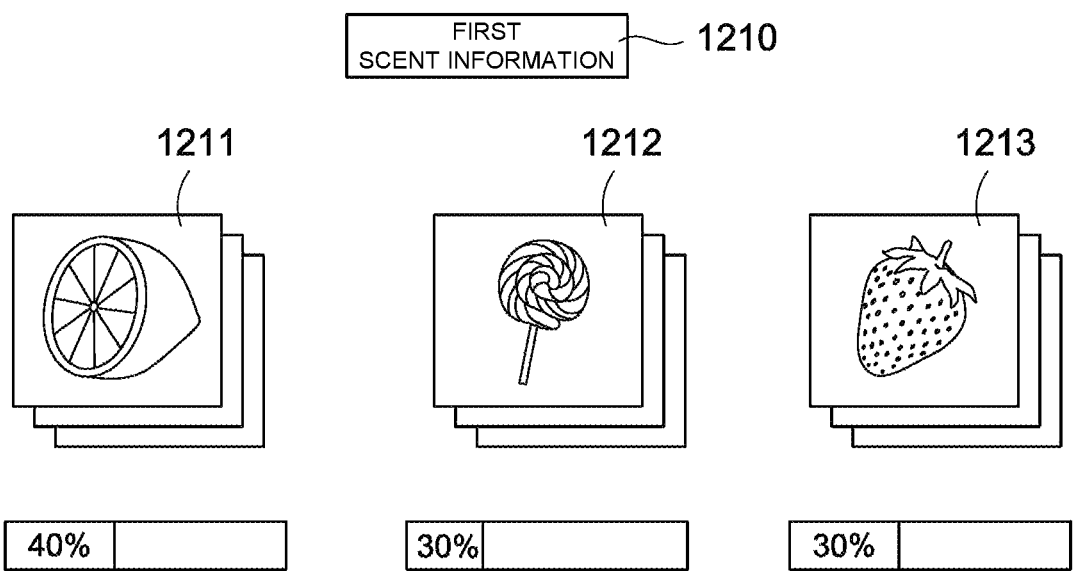
FIG. 4 is the first embodiment of the schematic diagram of the scent formula.

Please further refer to FIG. 4, which is the first embodiment of the scent formula diagram of the present disclosure. In the present disclosure, the scent information 121 mainly records the corresponding ingredient of a scent. For example, as shown in FIG. 4, the first scent information 1210 corresponds to a special scent, and the special scent is composed of 40% of the first ingredient 1211 (for example, citrus), 30% of the second ingredient 1212 (for example, sugar), and 30% of the third ingredient 1213 (for example, strawberry).

If the scent diffusion device (the scent diffusion device 2 shown in FIG. 1) is equipped with the first ingredient 1211, the second ingredient 1212, and the third ingredient 1213, when the scent diffusion device 2 receives the first scent information 1210, the first ingredient 1211, the second ingredient 1212, and the third ingredient 1213 can be blended according to the proportion mentioned above, thereby generating and diffusing the scent corresponding to the first scent information 1210. In this way, the user can obtain an olfactory experience through the scent diffusion device 2.

Figure 3A:
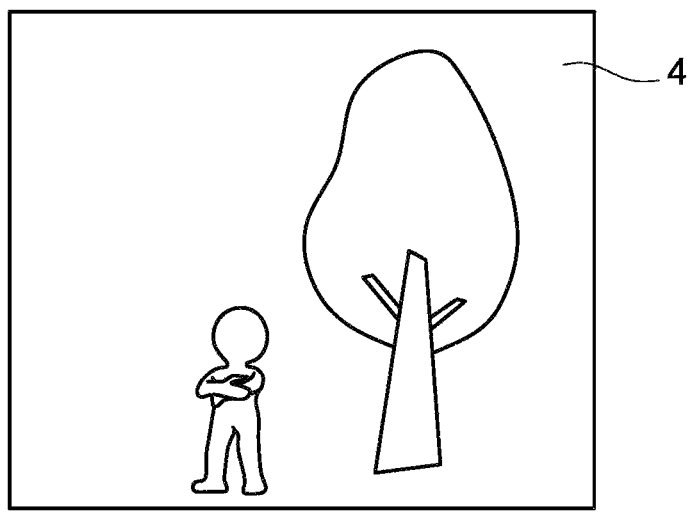
FIG. 3A is the first action step of the first embodiment of the method for adding scent information.

Returning to FIG. 1, the tagging program 11 is mainly installed and executed in the electronic device 1, and the electronic device 1 can open the digital photograph to be edited through the tagging program 11 (for example, the digital photograph 4 shown in FIG. 3A).

Figure 2:
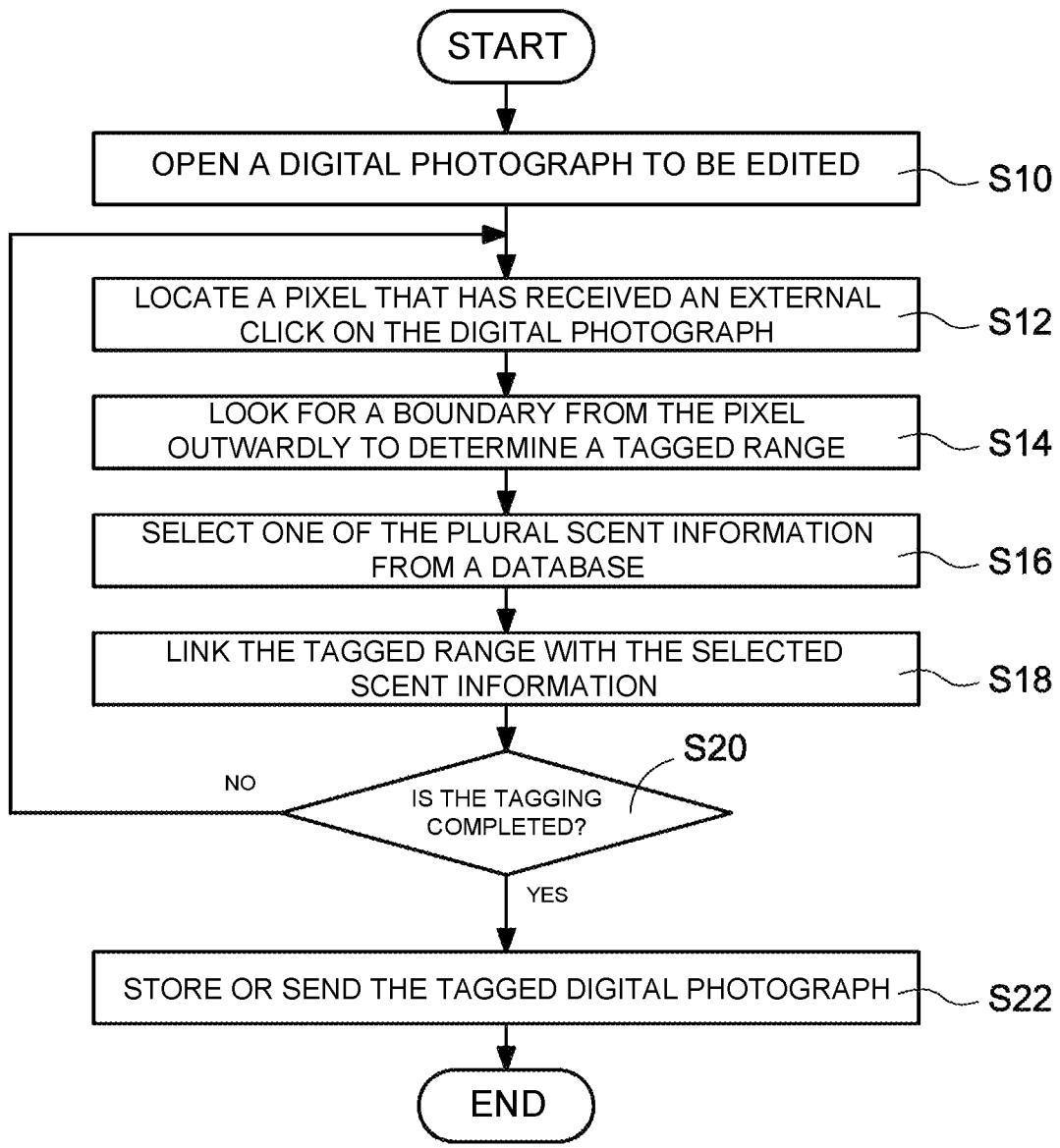
FIG. 2 is the first embodiment of the flow chart for adding scent information.

Please also refer to FIG. 2, which is the first embodiment of the flowchart for adding scent information. When the user wants to add scent information to a digital photograph, the tagging program 11 in the electronic device 1 can be used to load and open the digital photograph to be edited (step S10), and display the opened digital photograph on the screen of the electronic device 1.

Next, the electronic device 1 receives an external click action performed by a finger, a mouse, or a stylus, etc. via an operating interface to select any position (in a unit of pixel) on the digital photograph. The tagging program 11 locates the pixel that has received the above-mentioned external click on the digital photograph (step S12) and uses the pixel as a starting point, looking for the boundary from the pixel to determine a tagged range (Step S14).

Specifically, the user may not be able to accurately select a valid range during manual clicking, which may cause adding error problems. For example, if the user's finger is too big, they might accidentally click on the unwanted pixels that are in close proximity to the target pixels. The present disclosure adopts the above-mentioned edge finding auxiliary method to overcome the problem of the imprecise clicking by the user. For another example, if the user's finger is too small, it is necessary to repeat multiple clicking actions to tag a larger area. The aforementioned edge finding auxiliary method can also effectively avoid repetitive clicking actions. In light of this, this embodiment seeks out the effective boundary from the selected pixel to expand the pixel into an effective tagged range on the digital photograph, thereby facilitating the tagging program 11 to confirm the correct location where the user intends to add a scent information.

After step S14, the tagging program 11 selects one of the plural scent information 121 from the database 12 (step S16) and links the tagged range with the selected scent information (step S18). Furthermore, the above-mentioned scent information 121 can be selected either by the user from the database 12, automatically selected from the database 12 by the tagging program 11, or composed in real time by the user during the adding action, so forth. (detailed description will be given later, and it is not limited to but as an example). Next, the tagging program 11 judges whether the user's tagging operation is completed or not.

In one embodiment, the user can click on a position (corresponding to a pixel) on the digital photograph to define a tagged range and attach a piece of scent information to the tagged range. In another embodiment, the user can click multiple locations (corresponding to multiple pixels) on the digital photograph to define multiple tagged ranges and add corresponding scent information to the tagged ranges. In this way, the digital photographs can be linked with multiple pieces of the same or different scent information simultaneously.

After the user has confirmed that the tagging is completed, the tagging program 11 can further store or send the tagged digital photograph (step S22). Specifically, after the digital photograph is tagged, the tagging program 11 can store the digital photograph in a portable storage device, or send the tagged digital photograph through the messaging software (such as Line, WhatsApp, WeChat, etc.) to another electronic devices, or upload and post the tagged digital photographs on the social network sites (such as Facebook, Instagram, Twitter, Snapchat, TikTok, etc.).

As mentioned above, another user can execute a diffusion program 110 through another electronic device 1 (such as a second electronic device) to receive and open the tagged digital photograph. In addition, the diffusion program 110 can control the scent diffusion device 2 which is connected to the second electronic device to generate and diffuse the scent corresponding to one or more pieces of scent information added to the digital photograph. In the present disclosure, the tagging program 11 and the diffusion program 110 refer to different functions in the same application program, but the tagging program 11 and the diffusion program 110 can also be two independent sets of application programs, either way is feasible.

It is worth mentioning that the scent may change with time and place. The adding system of the present disclosure may further include a cloud database 3, which is connected to the electronic device 1 via a network. The cloud database 3 can automatically compose various scent ingredients through internet search, administrator settings, or machine learning and generate corresponding plural scent information accordingly. In the present disclosure, the tagging program 11 can be connected to the cloud database 3 through the electronic device 1 to regularly/irregularly update the plural scent information 121 in the database 12.

In another embodiment, the user can compose one or more kinds of scent information by themselves and store it in the database 12 or upload it to the cloud database 3. Furthermore, the user can also immediately modify the ingredients of the scent to be added to generate the above-mentioned scent information when performing the adding action, and then add the generated scent information to the tagged range. In other words, the adding method of the present disclosure has the function of selecting pre-composed scent information from the database 12 to perform the adding action, and it also has the function of performing the adding action based on the scent information composed by the user in real time.

Figure 3B:
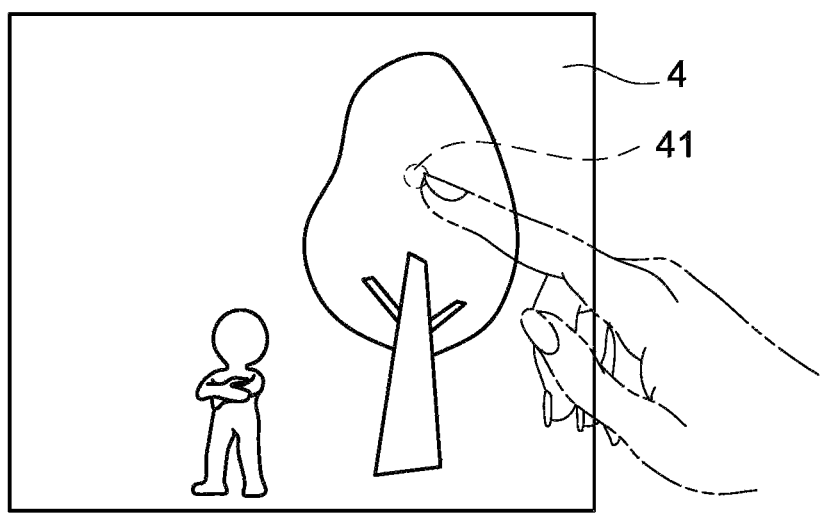
FIG. 3B is the second action step of the first embodiment of the method for adding scent information.

Please refer to FIG. 3A to 3F, which are respectively the first action step to the sixth action step of the first embodiment of the scent information adding method. First, as shown in FIG. 3A, the electronic device 1 can open the digital photograph 4 to be edited by executing the tagging program 11. Then, as shown in FIG. 3B, the user can perform an external click action on the digital photograph 4, and the tagging program 11 locates the pixel 41 that has been clicked by the user to determine the actual position clicked by the user.

Figure 3C:
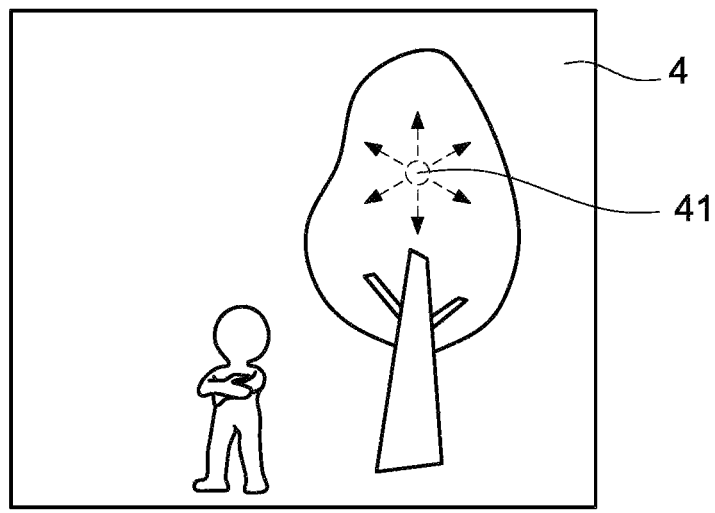
FIG. 3C is the third action step of the first embodiment of the method for adding scent information.
Figure 3D:
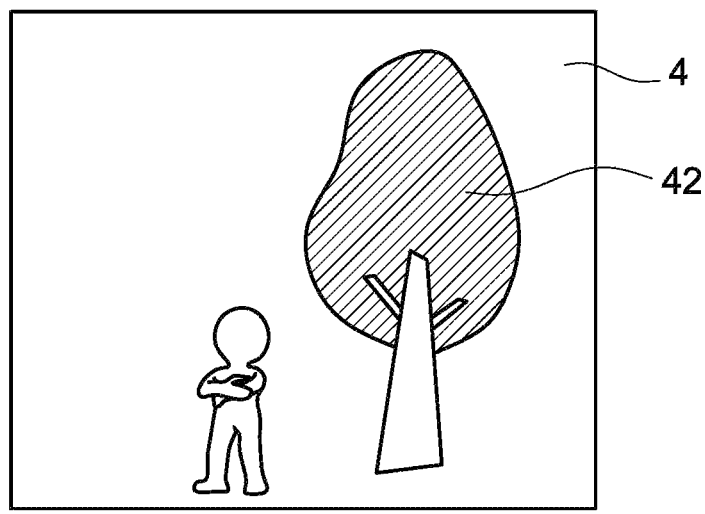
FIG. 3D is the fourth action step of the first embodiment of the method for adding scent information.
Figure 3E:
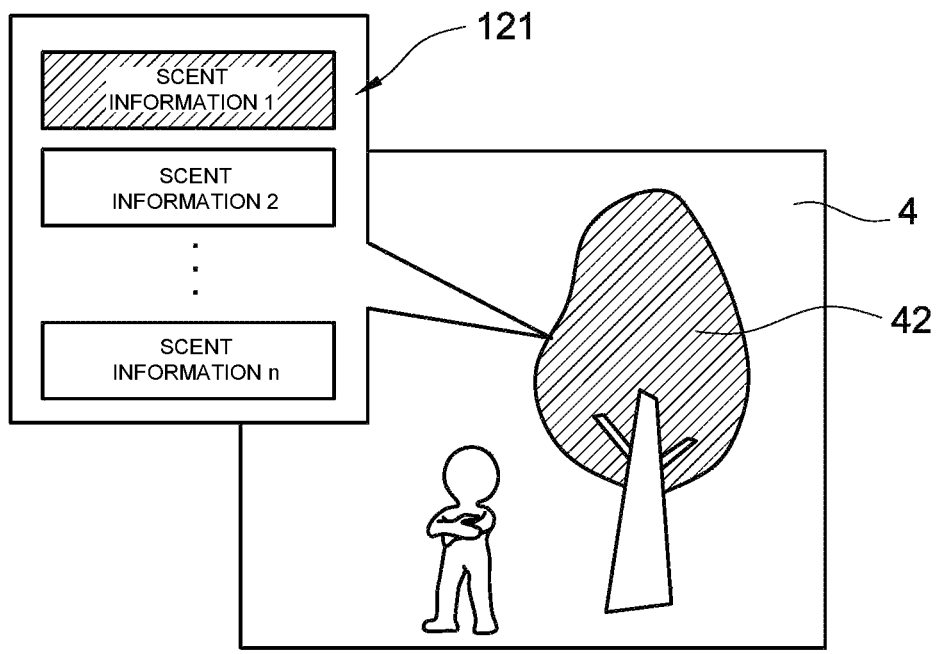
FIG. 3E is the fifth action step of the first embodiment of the method for adding scent information.
Figure 3F:
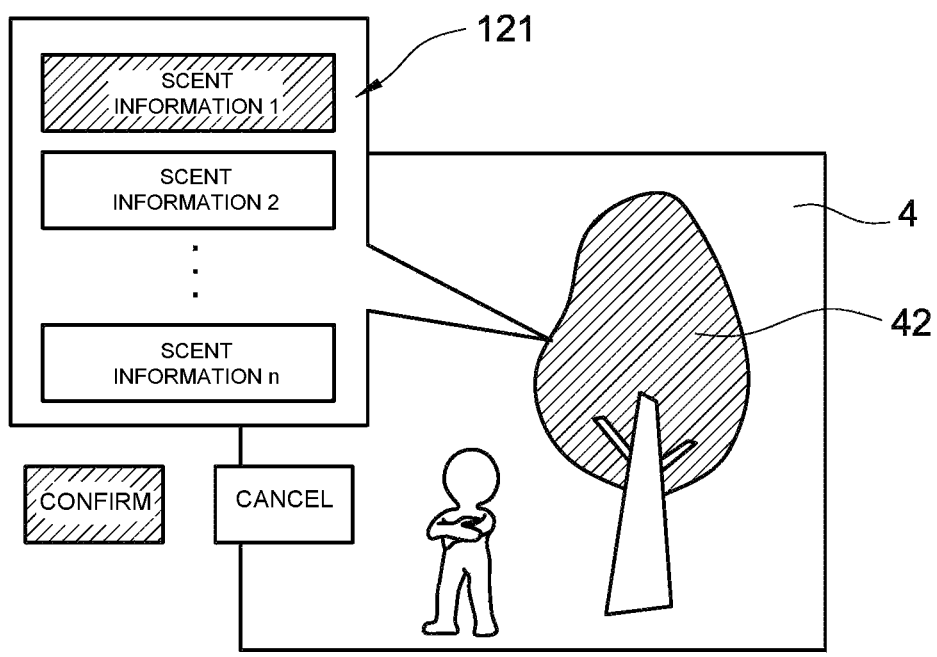
FIG. 3F is the sixth action step of the first embodiment of the method for adding scent information.

Next, as shown in FIG. 3C and FIG. 3D, the tagging program 11 searches for the effective boundary from the pixel point 41 outwardly, so as to expand the pixel point 41 into an effective tagged range 42. Next, as shown in FIG. 3E, the tagging program 11 can accept the user's operation to select one piece of scent information 121 from the plural scent information 121 which is stored in the database 12 (selecting scent information 1 in FIG. 3E as an example). And as shown in FIG. 3F, when the user presses the confirmation button displayed on the electronic device 1, the tagging program 11 can link the selected tagged range 42 with the selected scent information 121, and further store or send the tagged digital photograph 4.

Figure 5:
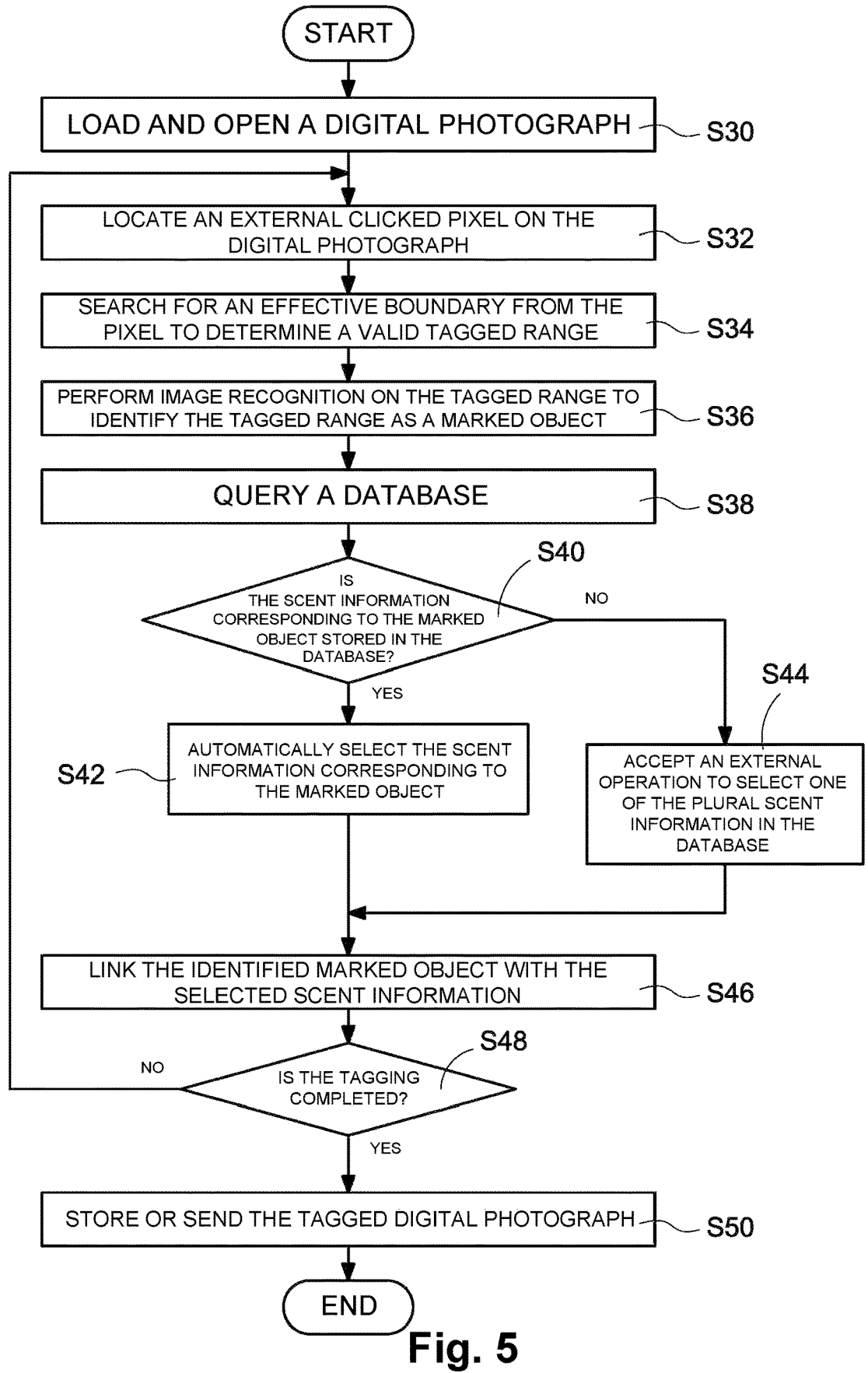
FIG. 5 is the second embodiment of the flow chart for adding scent information.

Please refer to FIG. 5, which is the second embodiment of the flowchart of adding scent information. In this embodiment, the electronic device 1 (for example, the first electronic device) firstly executes the tagging program 11 and loads and opens a digital photograph by the tagging program 11 (step S30). Next, after the digital photograph is clicked by the user, the tagging program 11 locates the clicked pixels on the digital photograph (step S32), and searches for the effective boundary from the pixels to determine a valid tagged range (step S34). The foregoing steps S30 to S34 are the same as or similar to the aforementioned steps S10 to S14 in FIG. 2 and will not be repeated here.

After step S34, the tagging program 11 further performs image recognition on the tagged range to identify the tagged range as a marked object (step S36). Specifically, in step S36, after the tagging program 11 determines a valid tagged range, it is determined whether the tagged range corresponds to a meaningful object through image recognition processing. For example, in the embodiment of FIG. 3D, the tagging program 11 may further perform image recognition on the tagged range 42 after determining an effective tagged range 42 in order to identify the object corresponding to the tagged range 42 (take leaves for example in FIG. 3D).

Next, the tagging program 11 queries the database 12 according to the identified marked object (step S38) and judge whether the scent information 121 corresponding to the marked object is stored in the database 12 or not (step S40). For example, if the tagging program 11 determines that a marked object is an apple after image recognition, then in step S40, the tagging program 11 judges whether the database 12 stores the scent information 121 corresponding to the scent of apple or not. After image recognition, if the program 11 determines that a marked object is grass, in step S40, the tagging program 11 judges whether the database 12 stores the scent information 121 corresponding to the scent of grass or not. However, the above description is only one embodiment of the present disclosure, and it is not limited thereto.

In step S40, if the tagging program 11 judges that the database 12 stores the scent information 121 corresponding to the marked object, then the tagging program 11 automatically selects the scent information 121 corresponding to the marked object (step S42) and recommends it to users (For example, a reminder window is displayed on the screen of the electronic device 1). In this way, the user can choose to directly use the scent information 121 recommended by the tagging program 11, select other scent information 121 from the database 12, or compose the scent information 121 by his willing.

Conversely, if the tagging program 11 judges that the database 12 does not have the scent information 121 corresponding to the marked object, the tagging program 11 further accepts the user's external operation to select one of the plural scent information 121 in the database 12 (Step S44), or the user can compose the scent information 121 by his willing.

It is worth mentioning that, in one embodiment, the first electronic device can also be connected to the scent diffusion device 2. In this embodiment, when the tagging program 11 recommends a piece of scent information 121, or the user selects a piece of scent information 121 in the database 12, or the user composes a piece of scent information 121, the tagging program 11 can directly transmit the scent information 121 to the scent diffusion device 2 which is connected to the first electronic device. By controlling the scent diffusion device 2, the transmitted scent information 121 can be diffused to the user for tryout. In this way, the user can determine whether to select this scent information 121, to reselect other scent information 121 in the database 12, or to recompose another scent information 121.

After step S42 and step S44, the tagging program 11 further links the identified marked object with the selected scent information 121 (step S46). Next, the tagging program 11 judges whether the user has completed the tagging operation of the digital photograph or not (step S48). If the user has not completed the tagging, the tagging program 11 executes step S32 to S46 again, so that the user continues to click the next pixel to tag the next marked object.

If the tagging program 11 judges that the user has completed the tagging, it can further store or send the tagged digital photograph (step S50).

As mentioned above, in one embodiment, the user can use the tagging program 11 to store the tagged digital photographs on a portable storage media. In another embodiment, the user can send the tagged digital photograph to other users through messaging software. In another embodiment, the user can upload and post the tagged digital photograph on the social network sites. In this way, other users can use another electronic device (such as a second electronic device) to open the tagged digital photograph to simultaneously obtain visual and olfactory experiences on the digital photograph.

Figure 6:
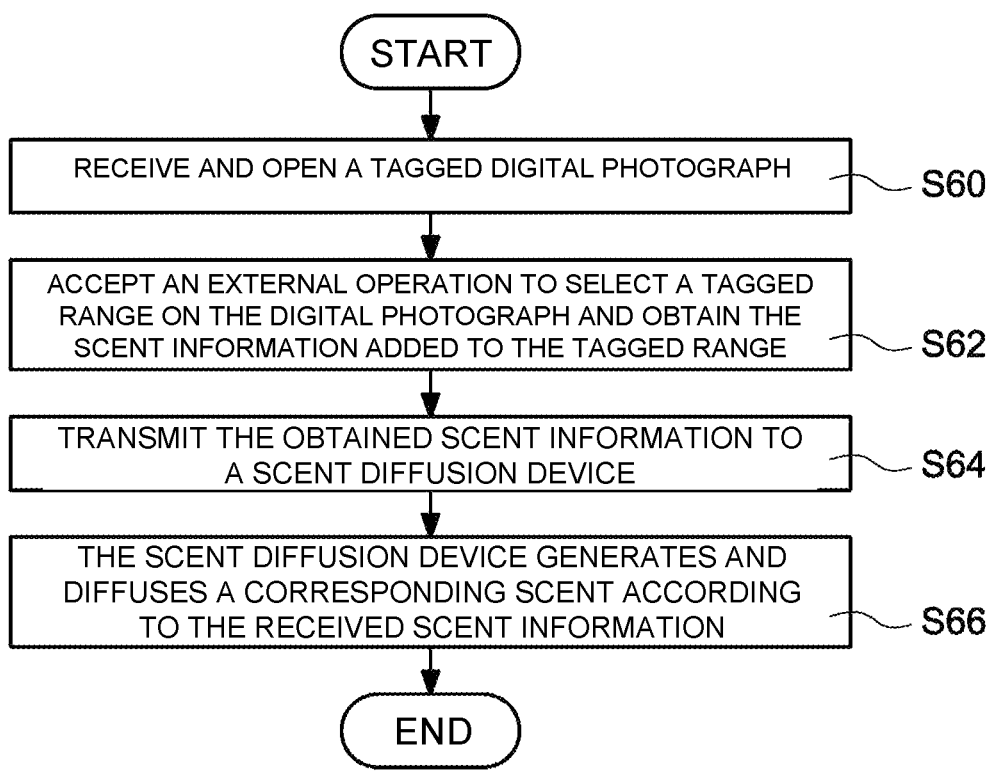
FIG. 6 is the first embodiment of the flow chart for scent diffusion.
Figure 7A:
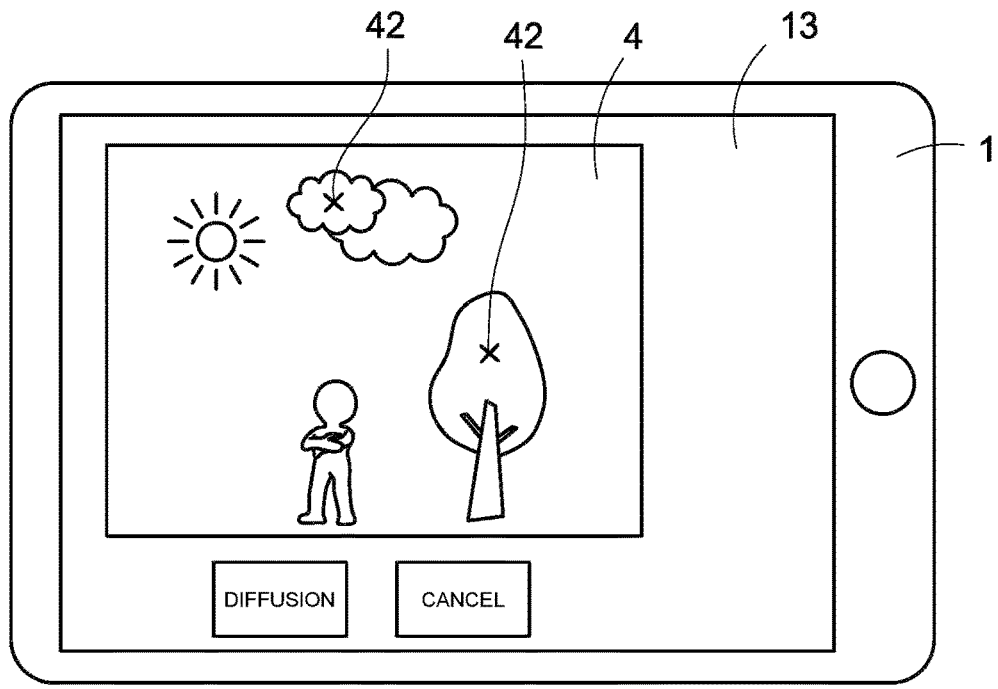
FIG. 7A is the first action step of the first embodiment of the scent diffusion method.
Figure 7B:
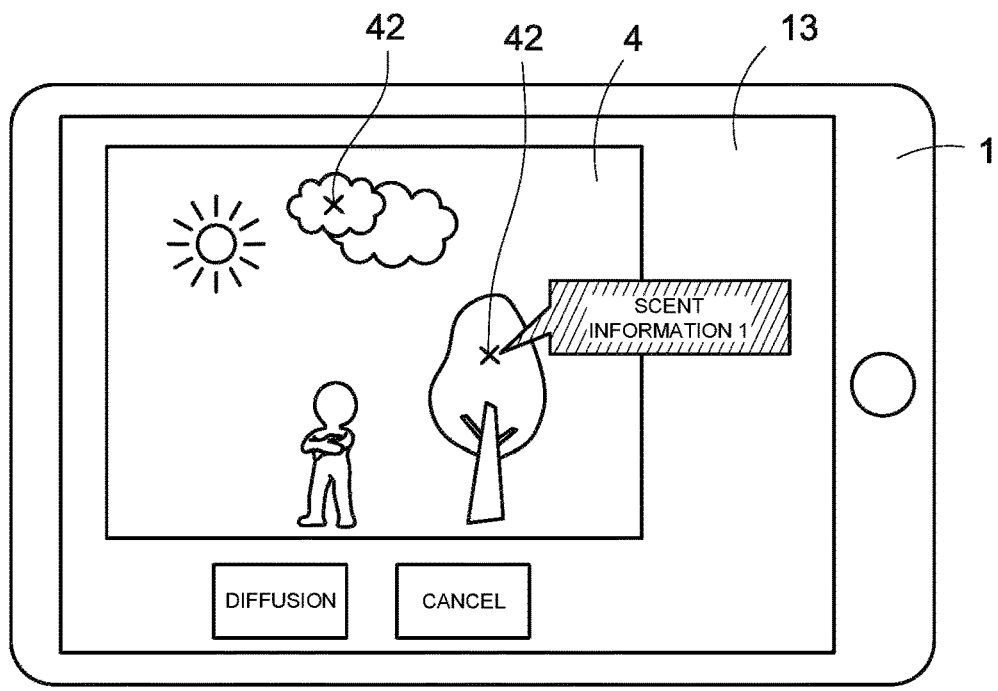
FIG. 7B is the second action step of the first embodiment of the scent diffusion method.
Figure 7C:
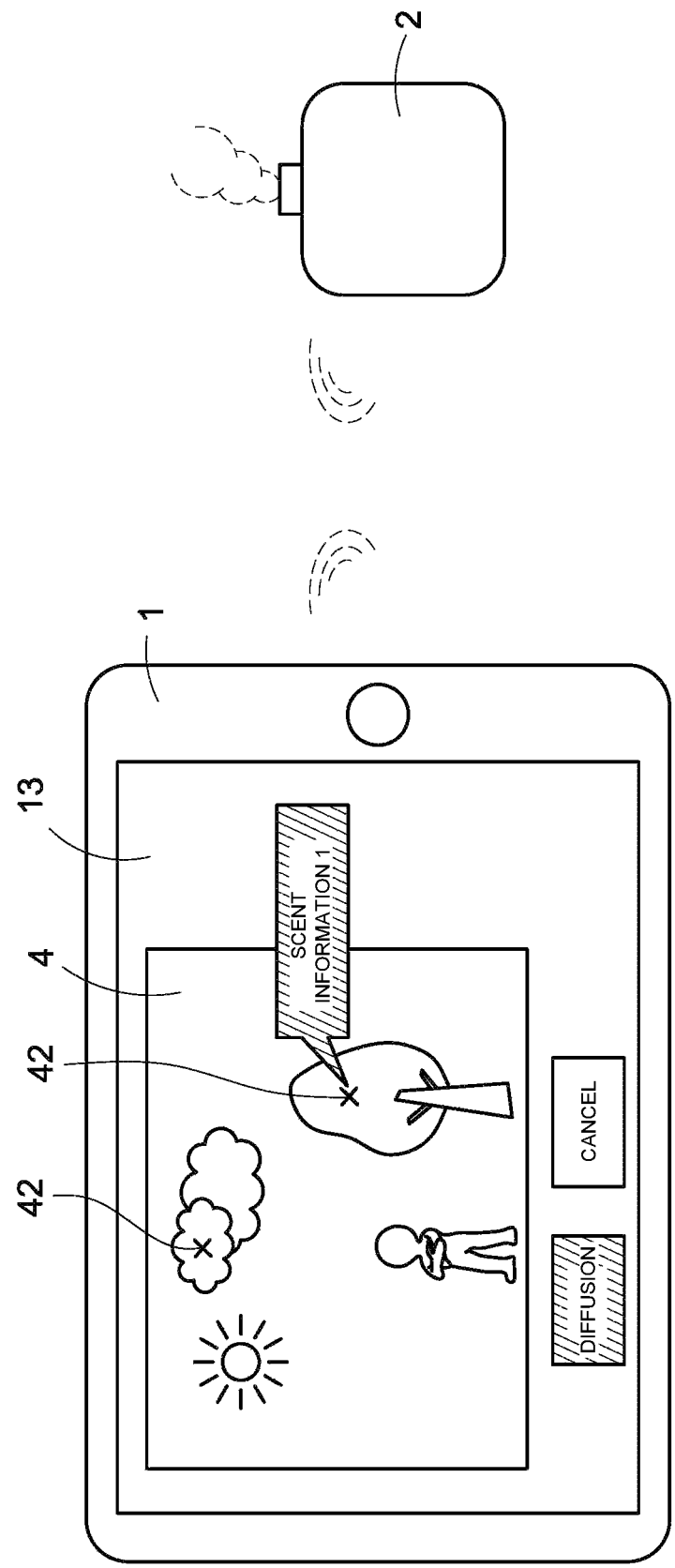
FIG. 7C is the third action step of the first embodiment of the scent diffusion method.

Please refer to FIG. 6 and FIG. 7A to 7C as well. FIG. 6 is the first embodiment of the scent diffusion flow chart of the present disclosure, and FIG. 7A to 7C are respective the first to the third action step of the first embodiment of the scent diffusion method.

When using the tagged digital photograph 4, the user firstly operates another electronic device 1 (for example, the second electronic device) and executes the diffusion program 110 installed in the electronic device 1 to receive and open the tagged digital photograph 4 (step S60). In this embodiment, the electronic device 1 is connected to the scent diffusion device 2 in a wired connection (such as a transmission cable) or a wireless connection (such as Wi-Fi, Bluetooth, Zigbee, NFC, etc.).

For example, a user can connect a portable storage medium storing a digital photograph 4 to the electronic device 1, so that the diffusion program 110 can load and open the digital photograph 4 stored in the portable storage medium. For another example, a user can connect to a social network site (such as Facebook) through the electronic device 1 and open the digital photograph 4 posted by other users on the social network site through the diffusion program 110.

After the diffusion program 110 opens the digital photograph 4, the opened digital photograph 4 can be displayed on the display screen 13 of the electronic device 1, and it is worth mentioning that the diffusion program 110 can simultaneously display one or more tagged ranges 42 on the display screen 13. In this way, the user can be reminded that the currently opened digital photograph 4 is a digital photograph 4 added with scent information. When the user touches any tagged range 42 on the digital photograph 4, no mis-selection will occur.

Then, the diffusion program 110 accepts the user's external operation through the display screen 13 of the electronic device 1 to select any tagged range 42 on the digital photograph 4 and obtain the scent information 121 added to the tagged range 42 (step S62). For example, in the embodiment of FIG. 7B, the user selects one of the tagged ranges 42 on the digital photograph 4, and the diffusion program 110 further obtains the scent information 121 added to this tagged range 42 (take the scent information 1 as an example).

If the user decides to diffuse the scent corresponding to the scent information 121 (for example, pressing the diffusion button shown in FIG. 7C), the diffusion program 110 transmits the obtained scent information 121 to the scent diffusion device 2 connected to the electronic device 1 (step S64). Thereby, the scent diffusion device 2 can receive the scent information 121 transmitted by the electronic device 1. Then, the scent diffusion device 2 generates and diffuses the corresponding scent according to the received scent information 121 (step S66).

In one embodiment, the scent diffusion device 2 directly diffuse the scent corresponding to the received scent information 121. In another embodiment, the scent diffusing device 2 generates the scent corresponding to the received scent information 121 which is composed by multiple different ingredients and then diffuse the generated scent.

In the above embodiment, the user can immediately press the diffusion button after selecting a tagged range 42 to make the scent diffusion device 2 immediately diffuse the corresponding scent.

In another embodiment, the diffusion program 110 can accept multiple external operations by the user to select multiple tagged ranges 42 on the digital photograph 4 and obtain the plural scent information 121 added to each tagged range 42 respectively. In other words, the diffusion program 110 can further judge whether the user has completed the selections or not after step S62. If the selections have not been completed yet, step S62 will be repeated, so that the user can select the next tagged range 42 again. In this way, when the user presses the diffusion button, the diffusion program 110 can simultaneously transmit the plural obtained scent information 121 to the scent diffusion device 2, and the scent diffusion device 2 can blend and diffuse multiple scents according to the plural received scent information 121. Through the above technical means, the present disclosure can make the scent smelled by the user more similar to the actual scent ambience at the moment while the digital photograph 4 was taken.

In the embodiment of FIG. 6, the diffusion program 110 directly selects one or more tagged ranges 42 on the digital photograph 4 by the user's operation and provides corresponding scent information 121 to the scent diffusion device 2 to make the scent diffusion device 2 diffuse the corresponding scent. However, in the present disclosure, the user can also trigger the diffusion program 110 to perform the above actions in other ways.

Figure 8:
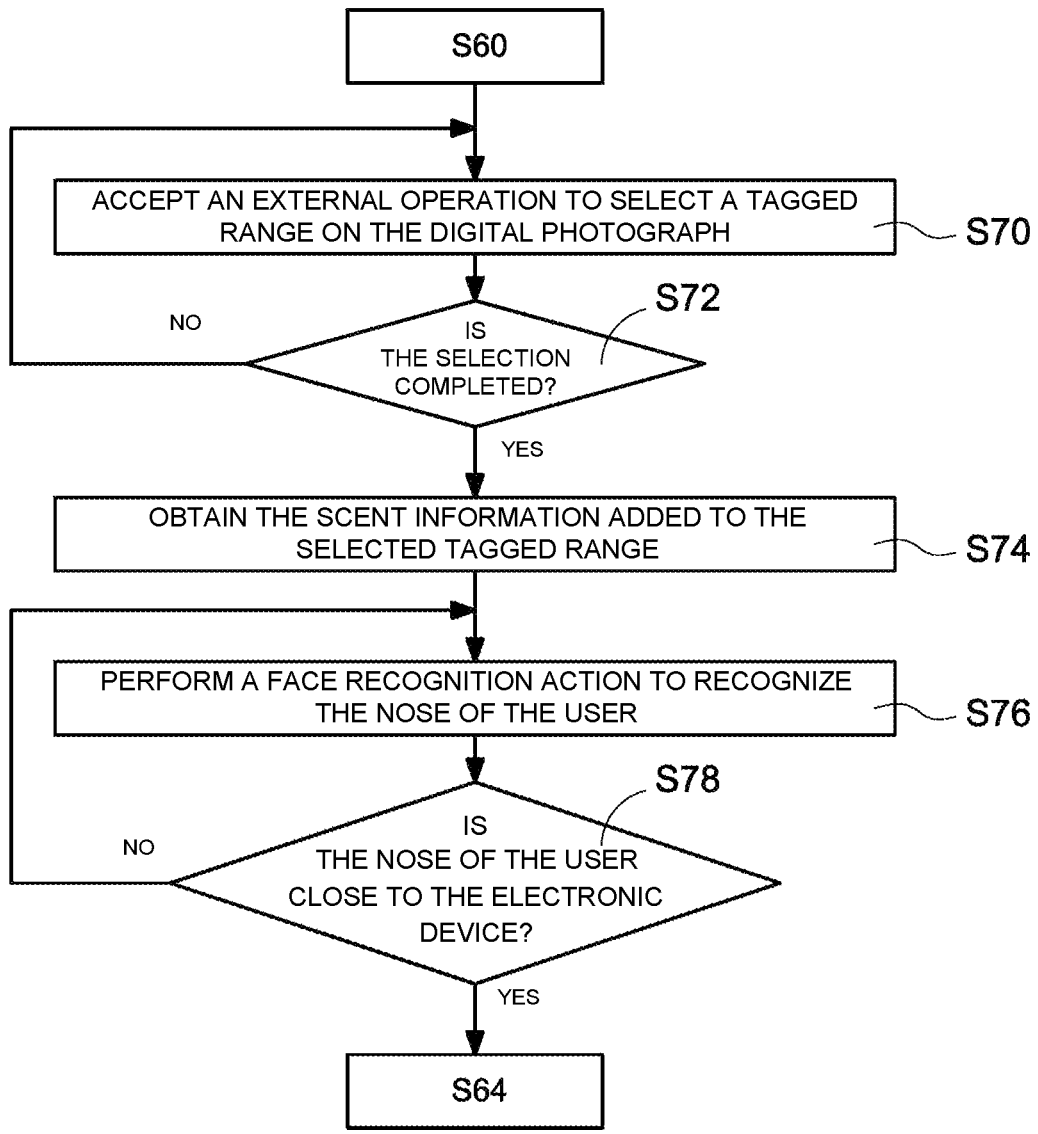
FIG. 8 is the second embodiment of the flow chart for scent diffusion.
Figure 9A:
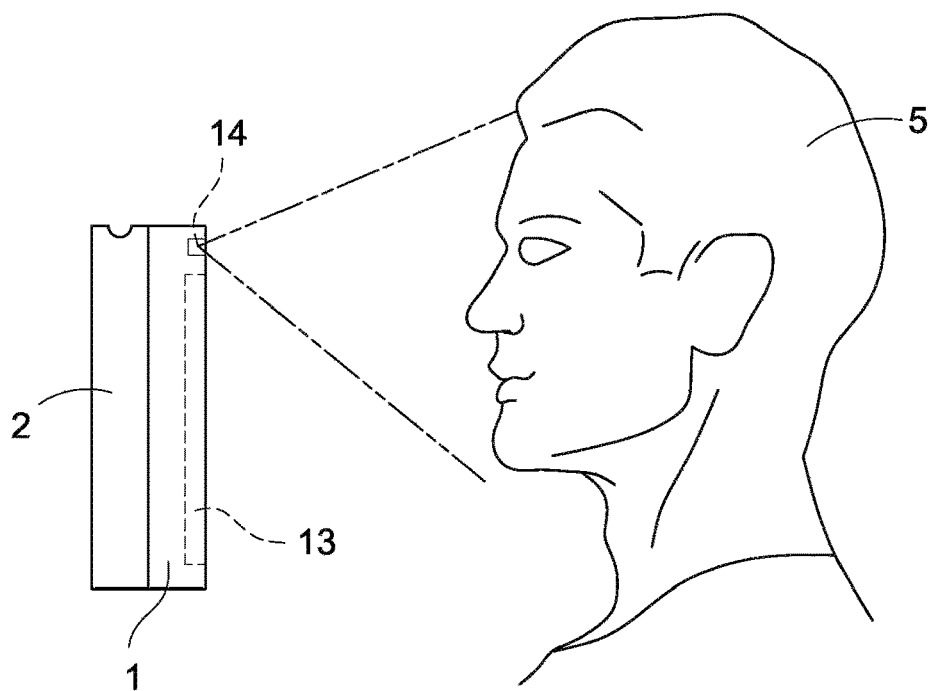
FIG. 9A is the first action step of the second embodiment of the scent diffusion method.
Figure 9B:
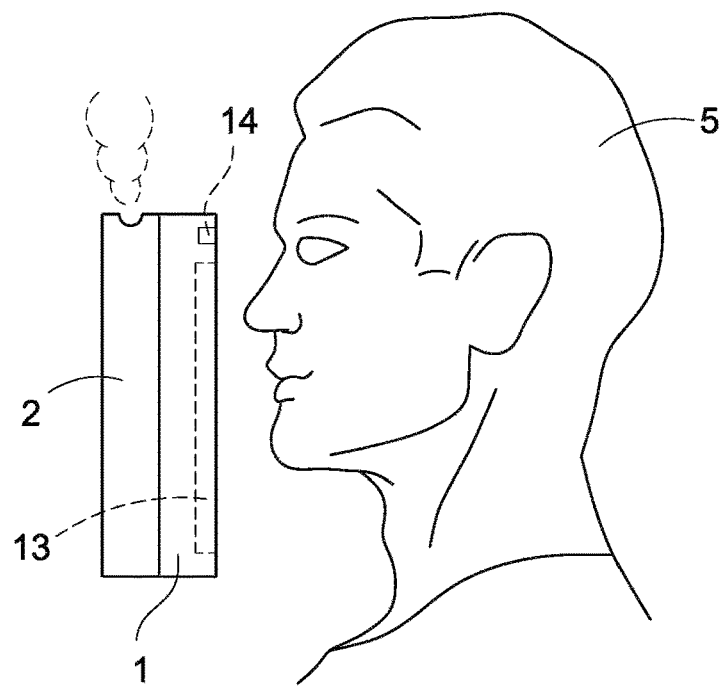
FIG. 9B is the second action step of the second embodiment of the scent diffusion method.

Please refer to FIG. 8 and FIG. 9A to 9B as well. FIG. 8 is the second embodiment of the scent diffusion flow chart of the present disclosure, and FIG. 9A to 9B are respective the first to the second action step of the second embodiment of the scent diffusion method. FIG. 8 is used to further explain step S62 in FIG. 6.

After opening the digital photograph 4 through step S60 in FIG. 6, the diffusion program 110 first accepts an external operation from a user 5 through the display screen 13 of the electronic device 1, so as to select any tagged range 42 on the digital photograph 4 (step S70). Next, the diffusion program 110 judges whether the user 5 has completed the selection or not (step S72). In other words, in this embodiment, the user 5 can select a single tagged range 42 on the digital photograph 4 (that is, the scent diffusing device 2 will only diffuse a single scent) or select multiple tagged ranges 42 on the digital photograph 4 (i.e., the scent diffusion device 2 will blend and diffuse multiple scents).

After the user 5 completes the selection (for example, presses the above-mentioned diffusion button), the diffusion program 110 obtains the scent information added to the selected tagged range 42 (step S74). Next, the diffusion program 110 performs a face recognition action on the user 5 through the sensor 14 on the electronic device 1 to recognize the nose of the user 5 (step S76). Then, the diffusion program 110 continues to judge whether the nose of the user 5 is close to the electronic device 1 or not (step S78). If the nose of the user 5 is not close to the electronic device 1 (for example, the distance from the electronic device 1 is not less than a threshold distance, such as 15 cm), the diffusion program 110 will not perform subsequent actions temporarily, but continuously detect the nose of the user 5.

If the diffusion program 110 judges that the nose of the user 5 is close to the electronic device 1 (for example, it is close to the display screen 13 of the electronic device 1 and the distance from the display screen 13 is less than the threshold distance), then the diffusion program 110 will execute step S64 shown in FIG. 6, so as to transmit the scent information 121 added to the selected tagged range 42 to the scent diffusion device 2. Finally, step S66 shown in FIG. 6 is further executed, that is, the scent diffusion device 2 generates and diffuses the corresponding scent according to the received scent information 121.

In the above embodiment, the diffusion program 110 allows the user 5 to first select the tagged range 42 of interest from the digital photograph 4, and when the nose of the user 5 approaches to the digital photograph 4, the scent diffusion device 2 will be subsequently controlled to diffuse the scent. In this way, the behavior of the user 5 approaching a physical object and then sniffing the physical object can be simulated, which makes the present disclosure more interesting and more realistic.

As shown in FIGS. 9A and 9B, in this embodiment, the scent diffusion device 2 can be the back cover of the electronic device 1 (for example, the electronic device 1 is a smart phone) or can be integrated with the electronic device 1 as a whole. In this embodiment, the outlet where the scent diffusion device 2 diffuses the scent is quite close to the display screen 13 of the electronic device 1. Therefore, when the nose of the user 5 is close to the electronic device 1, the user 5 can clearly smell the scent diffused from the scent diffusion device 2.

In the above-mentioned embodiment, the sensor 14 of the electronic device 1 can be for example, a proximity sensor, a flood illuminator, a dot projector, and an infrared camera. Specifically, after step S74, the electronic device 1 can control the proximity sensor thereon to sense whether an object is approaching or not and activate the flood illuminator when the object approaches. After the flood illuminator is activated, it emits non-structured light to detect the contour of the face, and the electronic device 1 receives the reflected light by the infrared camera to obtain the image information. In this way, the electronic device 1 can determine whether the object is a human face or not based on the obtained image information.

If the electronic device 1 determines that the object is not a human face, the electronic device 1 will terminate further actions.

If the electronic device 1 determines that the object is a human face, the electronic device 1 further controls the dot projector on it to project a plurality of infrared light spots (for example, 30,000) to the human face and receive the reflected light through the infrared camera to collate the facial information. Therefore, the electronic device 1 can recognize the nose position of the user 5 from the obtained facial information, and then judge whether the nose of the user 5 is close to the electronic device 1 or not. In this way, the diffusion program 110 can perform subsequent actions after judging that the nose of the user 5 is close to the electronic device 1 (and the distance from the electronic device 1 is less than the threshold distance).

Figure 10:
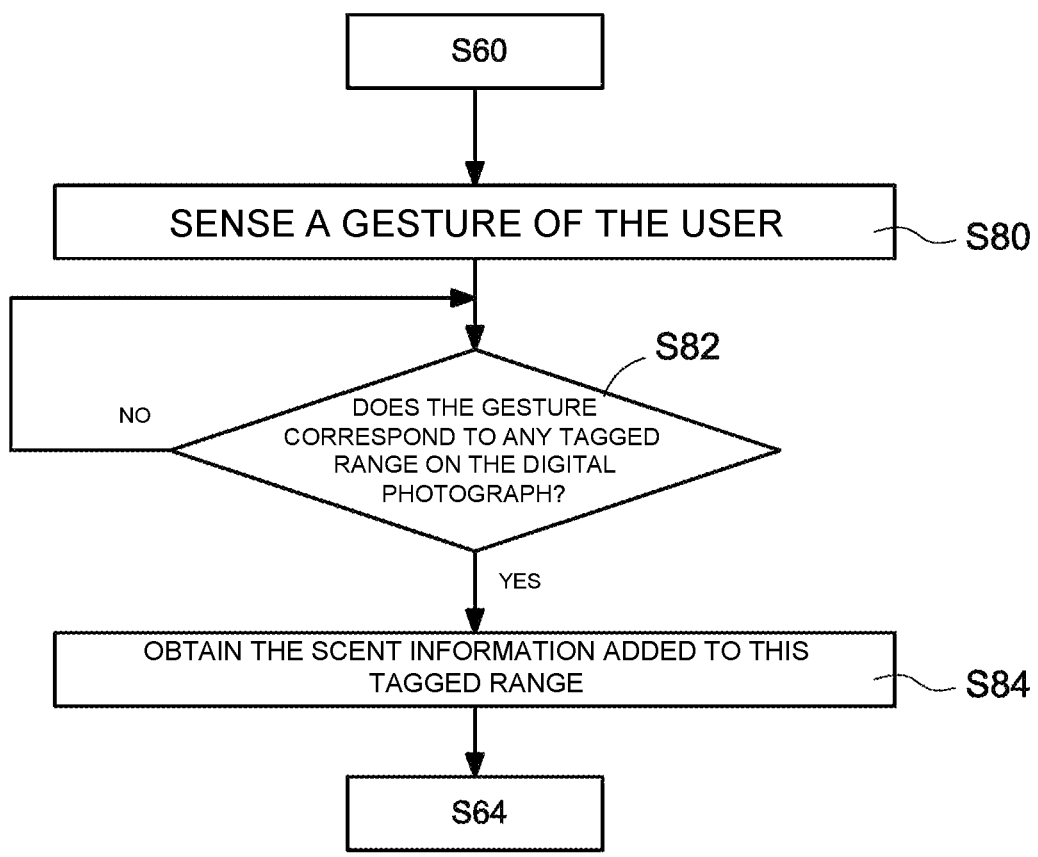
FIG. 10 is the third embodiment of the flow chart for scent diffusion.
Figure 11:
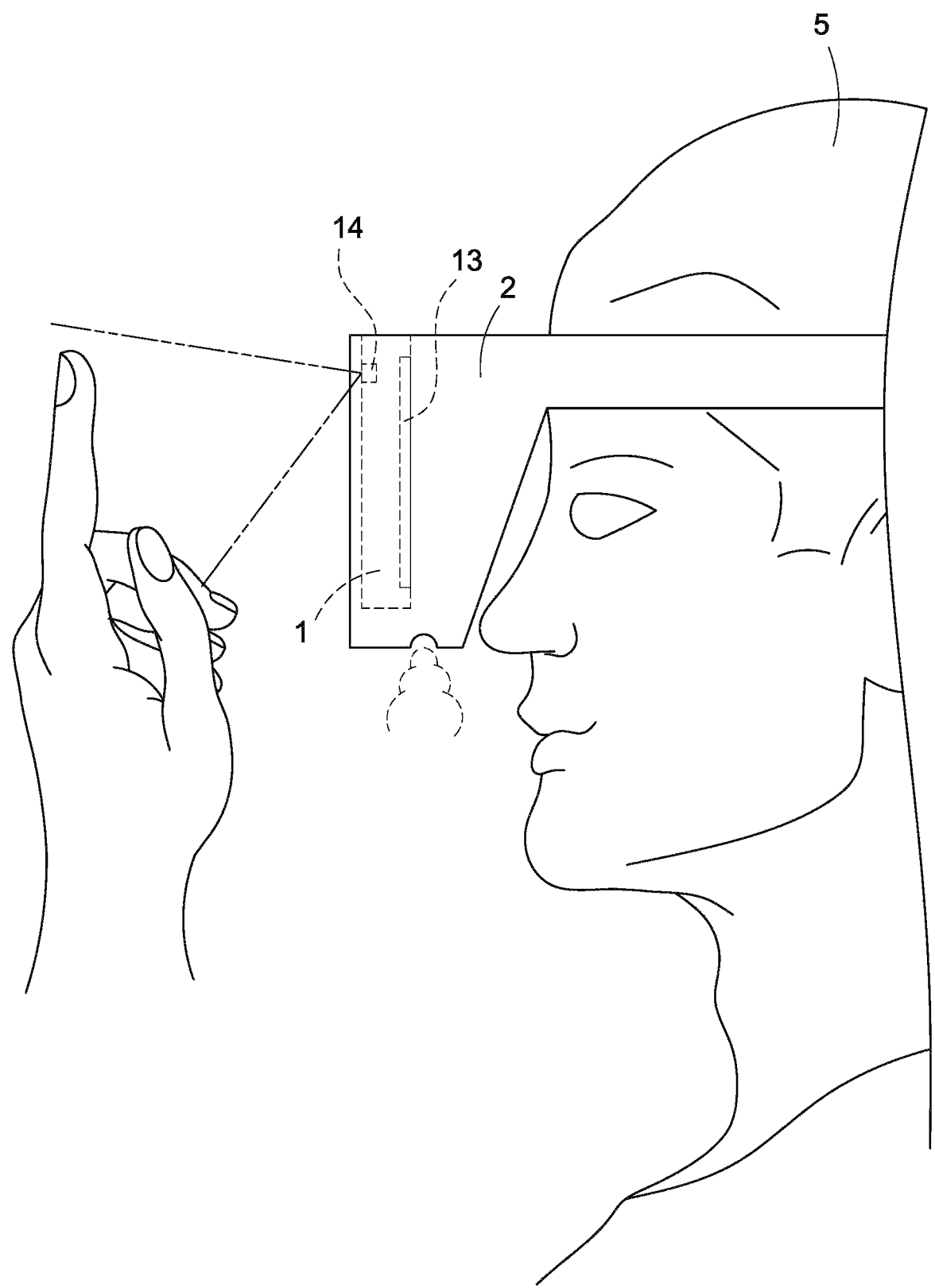
FIG. 11 is the third embodiment of the scent diffusion method.

Please refer to FIG. 10 and FIG. 11 as well. FIG. 10 is the third embodiment of the scent diffusion flow chart of the present disclosure, and FIG. 11 is the third embodiment of the scent diffusion method of the present disclosure. FIG. 10 is used to further explain step S62 in FIG. 6.

As shown in FIG. 11, in this embodiment, the scent diffusion device 2 can be a Virtual Reality (VR)/Augmented Reality (AR) helmet or glasses, and the electronic device 1 is installed on the scent diffusion device 2 or integrated with the scent diffusion device 2 as a whole.

In this embodiment, the user 5 is unable to directly touch the display screen 13 of the electronic device 1 with a finger or other input peripherals. Instead, after the electronic device 1 opens the digital photograph 4 through the diffusion program 110 (i.e., executes step S60 shown in FIG. 6), the diffusion program 110 senses a gesture of the user 5 through the sensor 14 on the electronic device 1 (step S80). When the gesture of the user 5 is sensed, it is determined whether the gesture corresponds to any tagged range 42 on the digital photograph 4 (step S82).

For example, when the user 5 performs the aforementioned tagging action, different tagged ranges 42 respectively correspond to different gestures (for instance, using the user's hand to make gestures of rock, paper, or scissors, etc.). After the diffusion program 110 senses the gesture of the user 5 in step S80, it can determine whether the sensed gesture corresponds to any tagged range 42.

For another example, since the scent diffusion device 2 in this embodiment is a VR/AR helmet or glasses, the diffusion program 110 can sense the hand position of the user 5 when the digital photograph 4 is opened and displayed on the display screen 13. The diffusion program 110 can further determine whether the hand position corresponds to the location of any tagged range 42 on the digital photograph 4 (for example, point the user's index finger to the location corresponding to any tagged range 42).

If the diffusion program 110 determines that the gesture of the user 5 cannot correspond to any tagged range 42 in step S82, then returns to step S80 to continuously sense the gesture of the user 5 through the sensor 14 of the electronic device 1. If the diffusion program 110 determines that the gesture of the user 5 can correspond to a tagged range 42, then further obtains the scent information 121 added to this tagged range 42 (step S84). Next, step S64 shown in FIG. 6 is executed to transmit the obtained scent information 121 to the scent diffusion device 2 by the diffusion program 110. Finally, step S66 shown in FIG. 6 is further executed, that is, the scent diffusion device 2 generates and diffuses the corresponding scent according to the received scent information 121.

In another embodiment, the scent diffusion device 2 (i.e., VR/AR helmet or glasses) and the electronic device 1 can also implement the above scent diffusion action through eye tracking and voice control.

Figure 12:
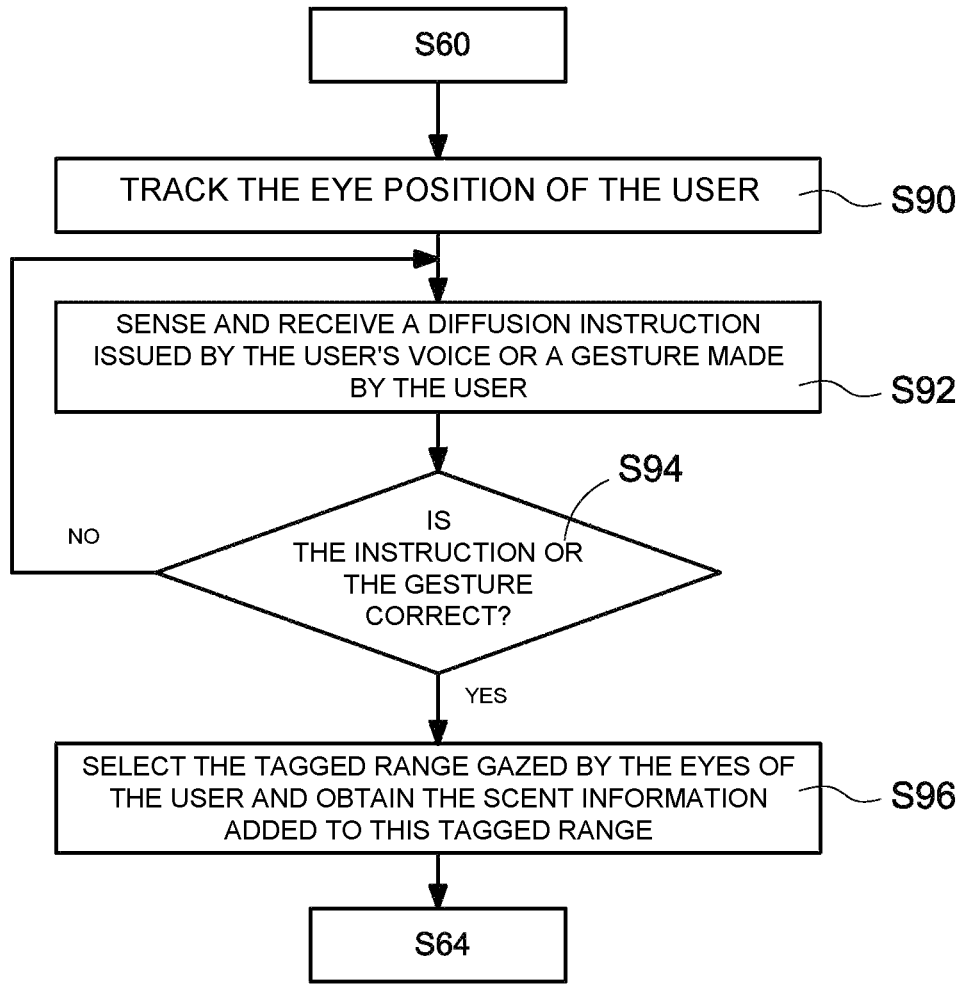
FIG. 12 is the fourth embodiment of the flow chart for scent diffusion.

Refer to FIG. 12, which is the fourth embodiment of the scent diffusion flow chart of the present disclosure. In this embodiment, after the electronic device 1 opens the digital photograph 4 through the diffusion program 110, the diffusion program 110 can track the eye position of the user 5 through another sensor (such as a camera lens) on the electronic device 1 (step S90) to determine which tagged range 42 on the digital photograph 4 the user 5's eyeball gazes on.

If the user 5 confirms that the tagged range 42 determined by the diffusion program 110 is correct, a corresponding diffusion instruction can be further issued by voice, or a corresponding gesture can be made by hand. The diffusion program 110 can sense and receive the diffusion instruction issued by the voice of the user 5 or the gesture made by the user 5 (step S92) through a sensor (such as the aforementioned sensor 14), and judge whether the diffusion instruction or the gesture is correct or not (step S94).

If the diffusion program 110 judges that the diffusion instruction or the gesture is correct, the tagged range 42 gazed by the eyes of the user 5 can be selected, and the scent information 121 added to this tagged range 42 can be obtained (step S96). Finally, the diffusion program 110 executes step S64 shown in FIG. 6 to transmit the obtained scent information 121 to the scent diffusion device 2 and control the scent diffusion device 2 to diffuse the corresponding scent.

Through the adding system and adding method of the present disclosure, users can easily create digital photographs with added scent information and share them with other users. In addition, other users can display digital photographs through electronic devices and diffuse scents added to the digital photographs through scent diffusion devices, thereby simultaneously experience a dual experience of vision and olfactory senses.

The above descriptions are only preferred specific examples of the present disclosure and are not limited to the scope of the present disclosure. Therefore, all equivalent changes made by using the content of the present disclosure are included in the scope of the present disclosure in the same way.

Furthermore, the described features of the disclosure may be combined in any suitable manner in one or more embodiments. One skilled in the relevant art will recognize, in light of the description herein, that the disclosure can be practiced without one or more of the specific features of a particular embodiment. In other instances, additional features may be recognized in certain embodiments that may not be present in all embodiments of the disclosure.

What is claimed is:

1. An adding system for adding scent information to a digital photograph, the add system comprising:
   a first electric device, comprising a display screen which is configured to display the digital photograph;
   a database storing a plurality of scent information; and
   a tagging program installing and executing in the first electric device, wherein the first electric device opens the digital photograph with the tagging program and locates a pixel on the digital photograph by external clicking,
   wherein the tagging program searches a boundary from the pixel outwardly to determine a tagged range,
   wherein the tagging program obtains a piece of scent information from the database among the plurality of scent information, and
   wherein the tagging program links the tagged range and the piece of scent information to complete a scent tagging; and the tagging program stores or sends the tagged digital photograph with the scent tagging.

2. The adding system as claim 1, further comprising a scent diffusion device connected to the first electronic device, and the tagging program determines the tagged range and obtains the corresponding scent information, then controls the scent diffusion device diffusing a scent corresponding to the scent information.

3. The adding system as claim 1, further comprising a cloud database connected to the first electronic device via a network, and the tagging program updates the plurality of scent information in the database through the cloud database.

4. The adding system as claim 1, further comprising:
a scent diffusion device; and
a diffusion program installed and executed in a second electronic device,
wherein the second electronic device is connected to the scent diffusion device and receives and opens the tagged digital photograph through the diffusion program;
wherein the diffusion program accepts an external operation to select the tagged range on the digital photograph and obtains the scent information added to the tagged range, and the diffusion program transmits the scent information to the scent diffusion device;
wherein the scent diffusion device generates and diffuses the corresponding scent according to the scent information.

5. The adding system as claim 4, wherein the diffusion program accepts the external operations to select a plurality of the tagged ranges on the digital photograph and obtains a plurality of the scent information added to the plurality of tagged ranges respectively, then the scent diffusion device blends and diffuses multiple scents according to the plurality of scent information.

6. The adding system as claim 4, wherein the diffusion program selects the tagged range and obtains the scent information added to the tagged range and then performs a face recognition through a sensor on the second electronic device and judges whether a user's nose is close to the second electronic device or not, and when it is judged that the user's nose is close to the second electronic device, the diffusion program controls the scent diffusion device to generate and diffuse the corresponding scent according to the scent information.

7. The adding system as claim 4, wherein the scent diffusing device is a back cover of the second electronic device or is integrated with the second electronic device as a whole.

8. The adding system as claim 4, wherein the scent diffusing device is a VR/AR helmet or glasses, and the second electronic device is installed on the scent diffusing device.

9. The adding system as claim 4, wherein the diffusion program opens the digital photograph and then senses a gesture of a user through a sensor of the second electronic device and selects the tagged range on the digital photograph according to the gesture.

10. The adding system as claim 4, wherein the diffusion program opens the digital photograph and then tracks an eye position of a user through a sensor of the second electronic device and receives the a diffusion instruction issued by the user's voice or a gesture made by the user, and when the diffusion program judges that the diffusion instruction or the gesture is correct, the tagged range gazed by the eye of the user is selected.

11. A method for adding scent information to a digital photograph, the method comprising steps of:
a) opening a digital photograph with a tagging program installed in a first electronic device;
b) locating a pixel that receives an external click on the digital photograph with the tagging program;
c) searching for a boundary from the pixel outwardly to determine a tagged range with the tagging program;
d) obtaining a piece of scent information from a database among a plurality of scent information or receiving the scent information composed by the user with the tagging program;
e) linking the tagged range with the piece of scent information with the tagging program; and
f) storing or sending the tagged digital photograph.

12. The method as claim 11 further comprising steps of:
providing a scent diffusion device connected to the first electronic device; and
Goldberg) after step d), controlling the scent diffusion device to diffuse a scent corresponding to the scent information with the tagging program.

13. The method as claim 11 further comprising steps of:
g) receiving and opening the tagged digital photograph with a diffusion program installed in a second electronic device, wherein the second electronic device is connected to a scent diffusion device;
h) accepting an external operation with the diffusion program to select the tagged range on the digital photograph and obtain the scent information added to the tagged range;
i) transmitting the scent information to the scent diffusion device with the diffusion program; and
j) generating and diffusing a corresponding scent according to the scent information with the scent diffusion device.

14. The method as claim 13, wherein in step h), the diffusion program accepts the external operations to select a plurality of the tagged ranges on the digital photograph and respectively obtains a plurality of the scent information added to the plurality of the tagged ranges; in step i), the diffusion program transmits the plurality of the scent information to the scent diffusion device; and in step j), the scent diffusion device blends and diffuses multiple scents according to the plurality of the scent information.

15. The method as claim 13, wherein step h) comprises steps of:
h11) accepting the external operation to select the tagged range on the digital photograph with the diffusion program;
h12) obtaining the scent information added to the tagged range;
h13) performing a face recognition through a sensor of the second electronic device to recognize a user's nose;
h14) judging whether the user's nose is in proximity to the second electronic device or not; and
h15) performing step i) and step j) when it is judged that the user's nose is in proximity to the second electronic device.

16. The method as claim 13, wherein step h) comprises steps of:
h21) sensing a user's gesture through a sensor of the second electronic device with the diffusion program;
h22) determining whether the user's gesture corresponds to any tagged range on the digital photograph; and
h23) when the user's gesture corresponds to any of the tagged ranges, selecting the corresponding tagged range according to the gesture and obtaining the scent information added to the tagged range and performing step i) and step j).

17. The method as claim 13, wherein step h) comprises steps of:

h31) tracking an eye position of a user through a sensor of the second electronic device with the diffusion program;
h32) receiving a diffusion instruction issued by the user's voice or a gesture made by the user;
h33) judging whether the diffusion instruction or the gesture is correct or not; and
h34) when it is judged that the diffusion instruction or the gesture is correct, selecting the tagged range gazed by the user's eyeball and obtaining the scent information added to the tagged range and performing step i) and step j).

\* \* \* \* \*